US008585662B2

(12) United States Patent
Conlon et al.

(10) Patent No.: US 8,585,662 B2
(45) Date of Patent: Nov. 19, 2013

(54) METHOD OF IMPLANTING A FLUID INJECTION PORT

(75) Inventors: Sean P. Conlon, Loveland, OH (US); Joshua Uth, Mason, OH (US); How-Lun Chen, San Diego, CA (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 0 days.

(21) Appl. No.: 13/030,176

(22) Filed: Feb. 18, 2011

(65) Prior Publication Data
US 2011/0144424 A1 Jun. 16, 2011

Related U.S. Application Data

(63) Continuation of application No. 12/333,365, filed on Dec. 12, 2008, now abandoned, which is a continuation of application No. 11/845,119, filed on Aug. 27, 2007, now abandoned, which is a continuation of application No. 10/858,898, filed on Jun. 1, 2004, now abandoned.

(51) Int. Cl.
*A61M 31/00* (2006.01)
*A61M 37/00* (2006.01)

(52) U.S. Cl.
USPC ....................... 604/288.01; 604/502

(58) Field of Classification Search
USPC .............. 604/288.01–288.04, 93.01, 174–75, 604/500, 502; 606/151, 153
See application file for complete search history.

(56) References Cited

U.S. PATENT DOCUMENTS

| 2,737,954 | A | | 3/1956 | Knapp |
|---|---|---|---|---|
| 3,371,352 | A | * | 3/1968 | Siposs et al. ................. 623/2.38 |
| 3,587,115 | A | | 6/1971 | Shiley |
| 3,686,740 | A | * | 8/1972 | Shiley ............................. 29/439 |
| 4,592,339 | A | | 6/1986 | Kuzmak et al. |
| 4,673,394 | A | * | 6/1987 | Fenton et al. ................. 604/175 |
| 5,213,574 | A | * | 5/1993 | Tucker ..................... 604/288.02 |
| 5,226,429 | A | | 7/1993 | Kuzmak |
| 5,304,204 | A | | 4/1994 | Bregen |
| 5,449,368 | A | * | 9/1995 | Kuzmak ........................ 606/157 |
| 5,540,648 | A | * | 7/1996 | Yoon ............................. 600/114 |
| 5,601,604 | A | | 2/1997 | Vincent |
| 5,653,718 | A | * | 8/1997 | Yoon ............................. 606/148 |
| 5,695,504 | A | | 12/1997 | Gifford, III et al. |
| 5,716,370 | A | * | 2/1998 | Williamson et al. .......... 606/153 |
| 5,771,903 | A | | 6/1998 | Jakobsson |
| RE36,176 | E | | 3/1999 | Kuzmak |

(Continued)

OTHER PUBLICATIONS

U.S. Appl. No. 60/478,763, filed Jun. 16, 2003. Conlon et al.

*Primary Examiner* — Kevin C Sirmons
*Assistant Examiner* — Andrew Gilbert
(74) *Attorney, Agent, or Firm* — Frost Brown Todd LLC

(57) ABSTRACT

A method for implanting an injection port within a patient. The method involves providing a port having a housing with a closed distal end, a open proximal end, a fluid reservoir therebetween, a needle penetrable septum attached to the housing about the opening, and at least one attachment mechanism mounted to the housing at a pivot point along an outer periphery of the housing. The attachment mechanism is an arcuate hook pivotable with respect to the housing, the arcuate hook having a length extending substantially at least 180° about the pivot point. The method further involves placing the distal end of the port adjacent tissue, and rotating the arcuate hook at least 180 degrees so that a free end of the hook extends into tissue and back out again.

19 Claims, 4 Drawing Sheets

(56) References Cited

U.S. PATENT DOCUMENTS

| | | | |
|---|---|---|---|
| 5,976,159 A * | 11/1999 | Bolduc et al. | 606/142 |
| 6,102,922 A | 8/2000 | Jakobsson et al. | |
| 6,106,550 A * | 8/2000 | Magovern et al. | 623/2.38 |
| 6,461,292 B1 | 10/2002 | Forsell | |
| 6,470,892 B1 | 10/2002 | Forsell | |
| 6,988,987 B2 | 1/2006 | Ishikawa et al. | |
| 7,037,305 B2 | 5/2006 | Kolata et al. | |
| 7,061,714 B1 | 6/2006 | Yu | |
| 7,374,557 B2 | 5/2008 | Conlon et al. | |
| 7,442,165 B2 | 10/2008 | Forsell | |
| 7,621,863 B2 | 11/2009 | Forsell | |
| 7,762,998 B2 * | 7/2010 | Birk et al. | 604/288.01 |
| 7,811,275 B2 * | 10/2010 | Birk et al. | 604/502 |
| 7,862,546 B2 * | 1/2011 | Conlon et al. | 604/175 |
| 7,892,200 B2 * | 2/2011 | Birk et al. | 604/93.01 |
| 7,909,804 B2 | 3/2011 | Stats | |
| 2004/0254537 A1 * | 12/2004 | Conlon et al. | 604/175 |
| 2005/0148956 A1 | 7/2005 | Conlon et al. | |
| 2005/0277899 A1 | 12/2005 | Conlon et al. | |
| 2006/0173423 A1 | 8/2006 | Conlon | |
| 2006/0178647 A1 | 8/2006 | Stats | |
| 2007/0293829 A1 | 12/2007 | Conlon et al. | |
| 2009/0093768 A1 | 4/2009 | Conlon et al. | |

* cited by examiner

METHOD OF IMPLANTING A FLUID INJECTION PORT

This application is a continuation of U.S. patent application Ser. No. 12/333,365, filed Dec. 12, 2008, now abandoned, published as U.S. Pub. No. 2009/0093768; which is a continuation of U.S. patent application Ser. No. 11/845,119, filed Aug. 27, 2007, now abandoned, published as U.S. Pub. No. 2007/0293829; which is a continuation of U.S. patent application Ser. No. 10/858,898, filed Jun. 1, 2004, now abandoned, published as U.S. Pub. No. 2005/0277899.

FIELD OF THE INVENTION

The present invention has application in conventional endoscopic and open surgical instrumentation as well as application in robotic-assisted surgery. The present invention has even further relation to adjustable surgically implantable bands, such as gastric bands for the treatment of obesity.

BACKGROUND OF THE INVENTION

The percentage of the world's population suffering from morbid obesity is steadily increasing. Severely obese persons are susceptible to increased risk of heart disease, stroke, diabetes, pulmonary disease, and accidents. Because of the effect of morbid obesity to the life of the patient, methods of treating morbid obesity are being researched.

Numerous non-operative therapies for morbid obesity have been tried with virtually no permanent success. Dietary counseling, behavior modification, wiring a patient's jaws shut, and pharmacological methods have all been tried, and failed to correct the condition. Mechanical apparatuses for insertion into the body through non-surgical means, such as the use of gastric balloons to fill the stomach have also been employed in the treatment of the condition. Such devices cannot be employed over a long term, however, as they often cause severe irritation, necessitating their periodic removal and hence interruption of treatment. Thus, the medical community has evolved surgical approaches for treatment of morbid obesity.

Most surgical procedures for treatment of morbid obesity may generally be classified as either being directed toward the prevention of absorption of food (malabsorption), or restriction of stomach to make the patient feel full (gastric restriction) The most common malabsorption and gastric restriction technique is the gastric bypass. In variations of this technique, the stomach is horizontally divided into two isolated pouches, with the upper pouch having a small food capacity. The upper pouch is connected to the small intestine, or jejunum, through a small stoma, which restricts the processing of food by the greatly reduced useable stomach. Since food bypass much of the intestines, the amount of absorption of food is greatly reduced.

There are many disadvantages to the above procedure. Typically the above mentioned procedure is performed in an open surgical environment. Current minimally invasive techniques are difficult for surgeons to master, and have many additional drawbacks. Also, there is a high level of patient uneasiness with the idea of such a drastic procedure which is not easily reversible. In addition, all malabsorption techniques carry ongoing risks and side effects to the patient, including malnutrition and dumping syndrome.

Consequently, many patients and physicians prefer to undergo a gastric restriction procedure for the treatment of morbid obesity. One of the most common procedures involves the implantation of an adjustable gastric band. Examples of an adjustable gastric band can be found in U.S. Pat. Nos. 4,592,339 issued to Kuzmak; RE 36176 issued to Kuzmak; 5,226,429 issued to Kuzmak; 6,102,922 issued to Jacobson and 5,601,604 issued to Vincent, all of which are hereby incorporated herein by reference. In accordance with current practice, a gastric band is operatively placed to encircle the stomach. This divides the stomach into two parts with a stoma in-between. An upper portion, or a pouch, which is relatively small, and a lower portion which is relatively large. The small partitioned portion of the stomach effectively becomes the patients new stomach, requiring very little food to make the patient feel full.

Once positioned around the stomach, the ends of the gastric band are fastened to one another and the band is held securely in place by folding a portion of the gastric wall over the band and closing the folded tissue with sutures placed therethrough thereby preventing the band from slipping and the encircled stoma from expanding. Gastric bands typically include a flexible substantially non-extensible portion having an expandable, inflatable portion attached thereto. The inflatable portion is in fluid communication with a remote injection site, or port. Injection or removal of an inflation fluid into or from the interior of the inflatable portion is used to adjust the size of the stoma either during or following implantation. By enlarging the stoma, the patient can eat more food without feeling as full, but will not lose weight as fast. By reducing the size of the stoma, the opposite happens. Physicians regularly adjust the size of stoma to adjust the rate of weight loss.

For most fluid injection ports for the above described bands are attached underneath the skin to the fascia of a patient. Such ports are often provided with suture holes and the port is sutured to the tissue. However, alternative means of attaching the port to the patient, such as using integral hooks, can be used as well. Such other means for attaching the port to a patient are described in commonly assigned and copending U.S. patent application Ser. Nos. 10/741,785 filed Dec. 19, 2003; 60/478,763 filed Dec. 19, 2003; 10/741,868 filed Dec. 30, 2003; all of which are hereby incorporated herein by reference.

SUMMARY OF THE INVENTION

In accordance with the present invention, there is provided a method for implanting an injection port within a patient. The method involves providing a port having a housing with a closed distal end, a open proximal end, a fluid reservoir therebetween, a needle penetrable septum attached to the housing about the opening, and at least one attachment mechanism mounted to the housing at a pivot point along an outer periphery of the housing. The attachment mechanism is an arcuate hook pivotable with respect to the housing, the arcuate hook having a length extending substantially at least 180° about the pivot, point. The method further involves placing the distal end of the port adjacent tissue, and rotating the arcuate hook at least 180 degrees so that a free end of the hook extends into tissue and back out again.

DETAILED DESCRIPTION OF THE DRAWINGS

The novel features of the invention are set forth with particularity in the appended claims. The invention itself, however, both as to organization and methods of operation, together with further objects and advantages thereof, may best be understood by reference to the following description, taken in conjunction with the accompanying drawings in which:

DETAILED DESCRIPTION OF THE INVENTION

Figure 1:
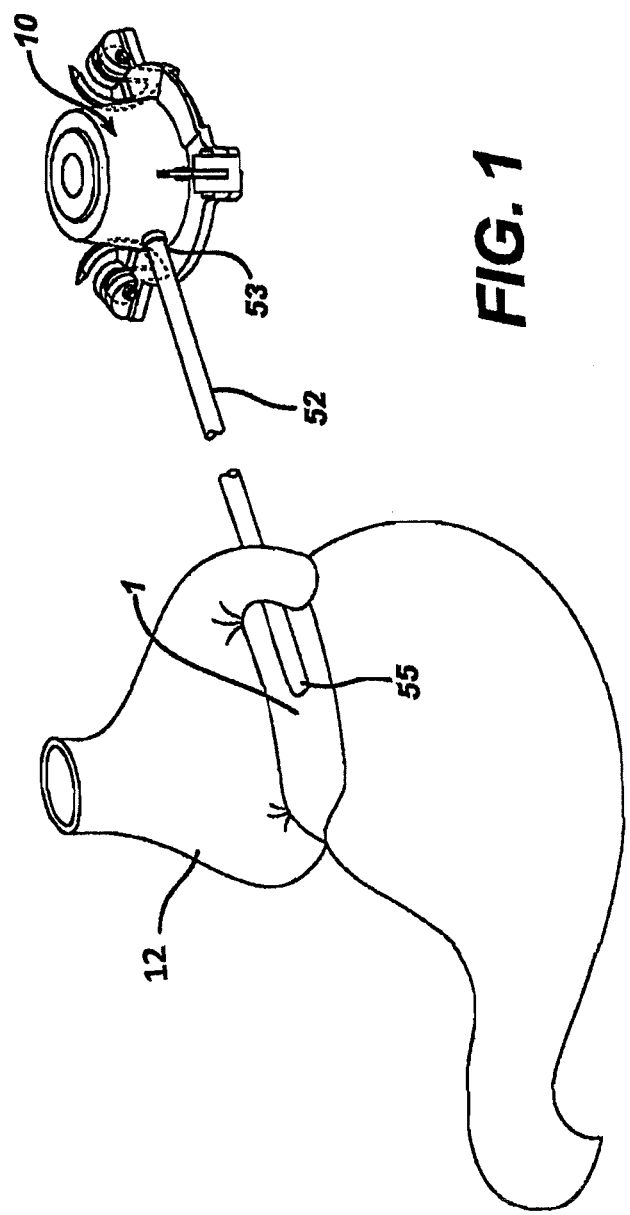
FIG. 1 is a perspective view of a surgically implantable fluid port made in accordance with the present invention, showing the port attached to an adjustable gastric band.

Referring now to the drawings wherein like numerals indicate the same elements throughout the views, as stated above there is shown in FIG. 1 an adjustable gastric band 1 of the type described in the above mentioned incorporated references. Band 1 is implanted within a body of a patient to surround the stomach 12. The inflatable portion of the band is in fluid communication with injection port 10 via a catheter tube 52. Tube 52 has a proximal end 53 attached to the port 10 and a distal end 55 attached to adjustable gastric band 1. Port 10 can be used for a wide range of devices in the medical field and not only for gastric bands. For example the port can also used for vascular access for drug delivery.

Figure 2:
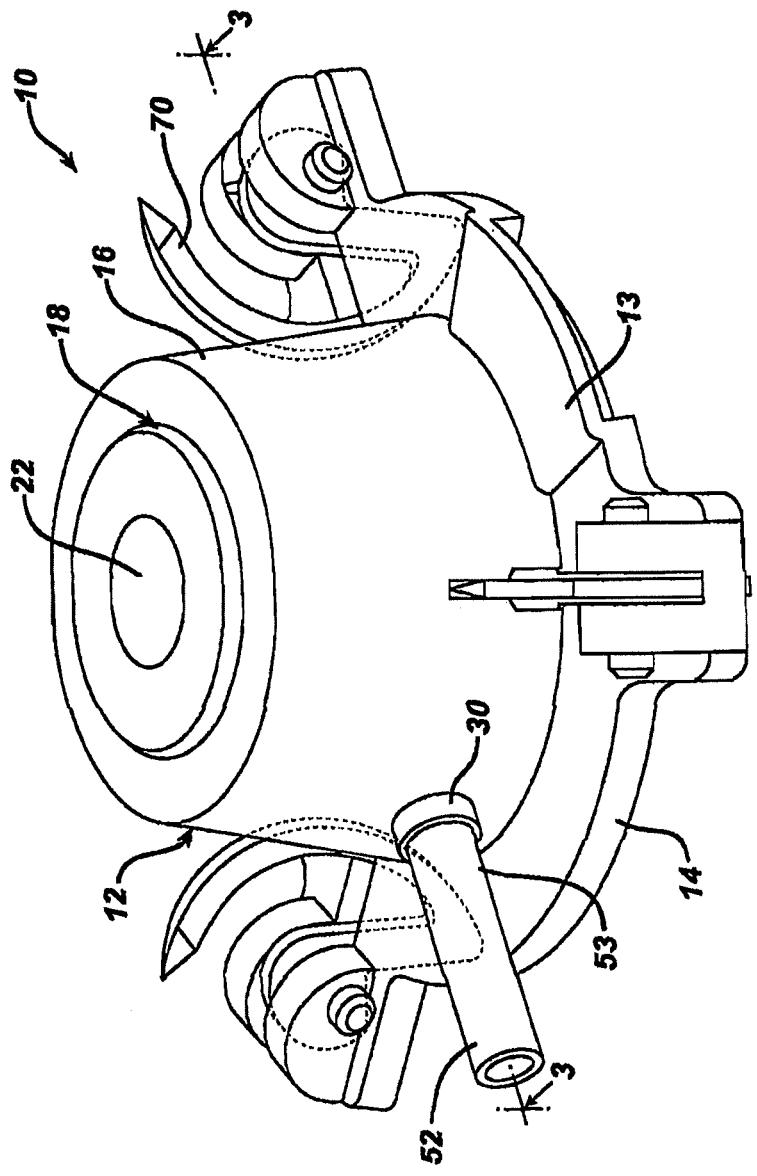
FIG. 2 is a perspective view of a surgically implantable fluid port made in accordance with the present invention.
Figure 3:
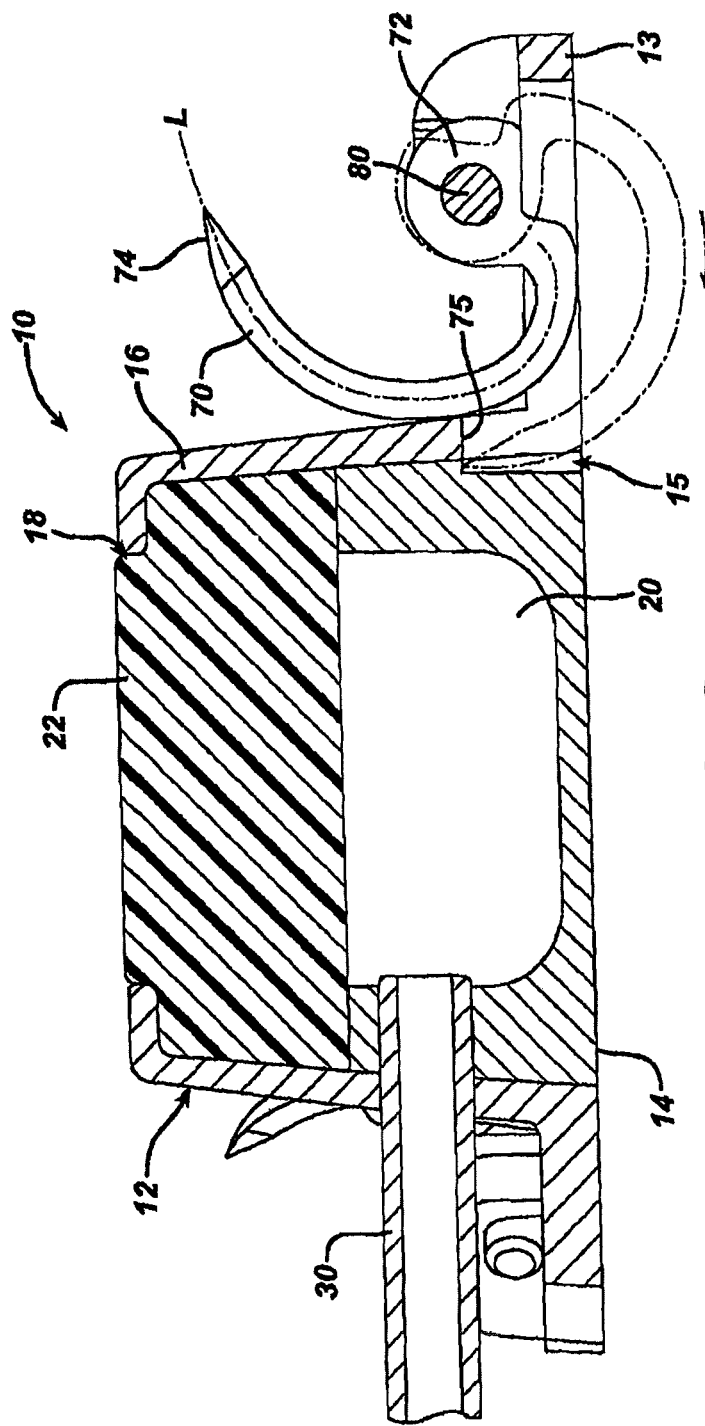
FIG. 3 is a cross section of the port shown in FIGS. 1 and 2, taken along line 3-3 in FIG. 2.

As seen from FIGS. 2 and 3, surgically implantable injection port 10 includes a housing 12. Housing 12 can be made from any number of materials including stainless steel, titanium, or polymeric materials. Housing 12 has a distal back portion or closed distal end 14 and a perimeter wall portion 16 extending proximally from the back portion 14 at an angle. Wall portion 16 defines a proximal opening or open proximal end 18, and a fluid reservoir 20 between opening 18 and back portion 14. The port includes a needle penetrable septum 22 attached to the housing about the opening 18 so as to cover the opening and seal the reservoir 20. Septum 22 can be made from any number of materials including silicone. Septum 22 is preferably placed in a proximal enough position such that the depth of the reservoir 20 is sufficient enough to expose the open tip of a needle, such as a Huber needle, so that fluid transfer can take place. Septum 22 is preferably arranged so that it will self seal after being punctured by a needle and the needle is withdrawn. In one embodiment, the septum is made from silicone which is under compression when attached to the housing. Port 10 further includes a catheter tube connection member 30, in fluid communication with reservoir 20.

Figure 4:
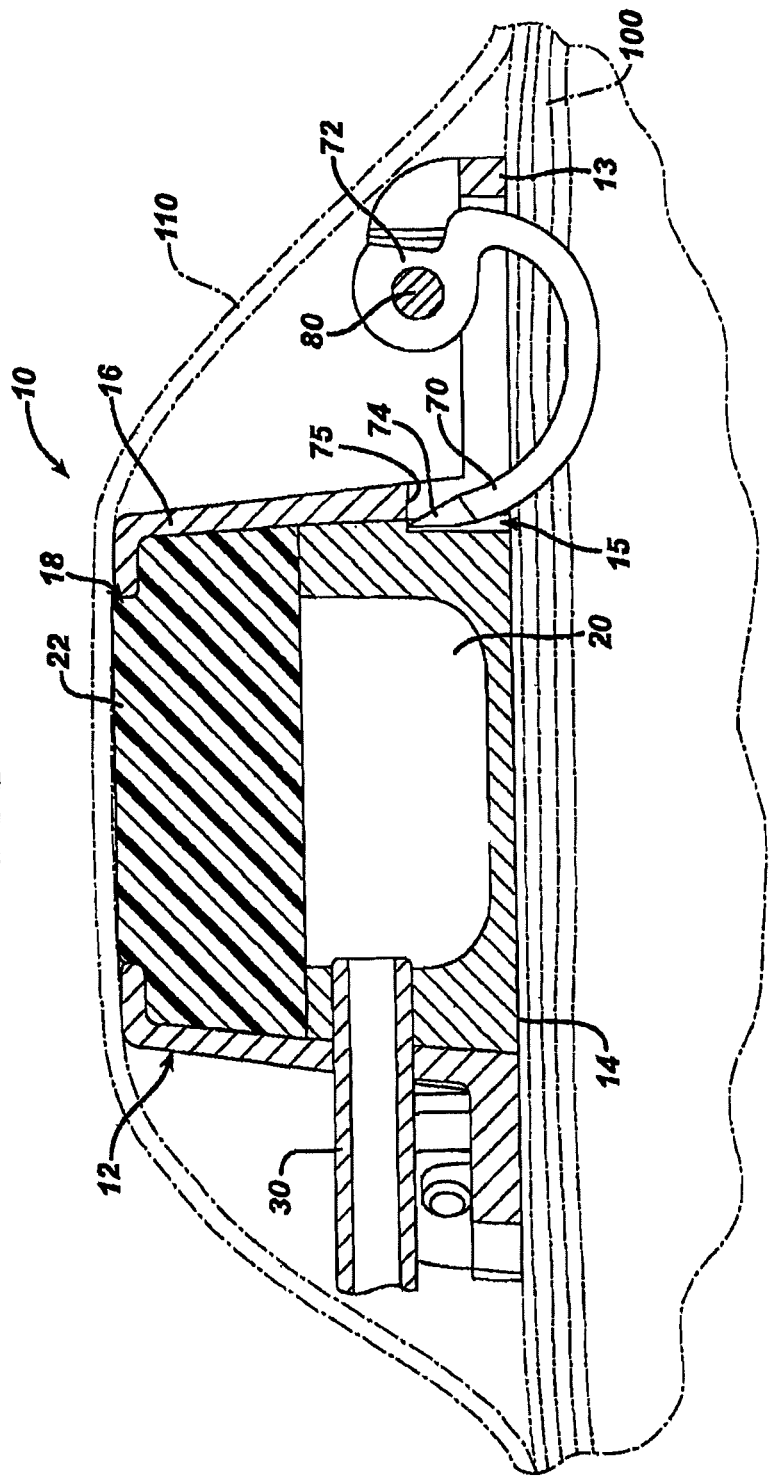
FIG. 4 is a view similar to that of FIG. 3 but showing the fluid port implanted within patient.

As seen from the figures, port 1 one or more attachment mechanisms 70. The figures herein show three attachment mechanisms all substantially identical and equally spaced from each other. Attachment mechanisms 70 are mounted to the housing 12 at a pivot point 80 along an outer periphery 13 of the housing 12. As seen from the figures, attachment mechanisms 70 are arcuate hooks pivotable with respect to the housing. Attachment mechanisms 70 have an arcuate length L extending substantially greater than 90°, and preferably at least 180° about the pivot point. Implantable surgical injection port 10 has an undeployed position, shown as a solid line in FIG. 3, and a deployed position, shown as the phantom line in FIG. 3 and in FIG. 4, wherein the port is attached to tissue. Attachment mechanisms 70 can be made from any number of materials including stainless steel, titanium or absorbable materials such as polyglactin and poliglecaprone.

Attachment mechanism 70 has a fixed end 72 pivotally attached to the housing 12 at pivot point 80. The design allows a surgeon to use forceps and drive the fastener through the tissue until the free end 74 rests against the flat 75. In this way the patient is protected from the sharp end of the tip. Attachment mechanism 70 also includes a free end 74 which has a sharp or pointed configuration. Housing 12 further includes at least one recessed portion 15 along its distal end 14. Recessed portion 15 is designed to receive the free end 74 of attachment mechanisms 70 when the port 1 is in its deployed position. This design prevents any exposure of the sharp free end to tissue after the port has been implanted.

The above described 180° hook or attachment mechanisms provide advantages over prior 90° or less hooks. As seen from FIG. 4, the above described attachment mechanism allows the hook to engage a greater area of tissue, and allows for two locking points, entry into and then out of the fascia. This provides for better sacrament of the port to the tissue. Further no "sharp" is exposed to the patient. A further advantage of the fastener configuration is that the fastener follows a constant radius when pushing through the tissue. By maintaining a constant radius the fastener never induces a compressive force onto the fascia. This should minimize pain because the fastener is not "compressing or squeezing" nerves.

In practice, the physician would create an incision in the skin 110 of a patient to expose the fascia according to well known surgical techniques. Thereafter, as seen from FIG. 4, the port 1 could be placed against the fascia 100 of the patient with the port in its undeployed position. Thereafter, the physician could rotate, manually or otherwise, the attachment mechanism substantially greater than 90° and preferably at least 180° so that the hook enters and then exits the fascia. The design allows a surgeon to use forceps and drive the fastener through the tissue until the free end 74 rests against the flat 75. In this way the patient is protected from the sharp end of the tip. This could be done for each attachment mechanism on the device. Thereafter, the catheter tube 52 would be connected to connection member 30, and the patient is sewn up.

It will become readily apparent to those skilled in the art that the above invention has equally applicability to other types of implantable bands. For example, bands are used for the treatment of fecal incontinence. One such band is described in U.S. Pat. No. 6,461,292 which is hereby incorporated herein by reference. Bands can also be used to treat urinary incontinence. One such band is described in U.S. Patent Application 2003/0105385 which is hereby incorporated herein by reference. Bands can also be used to treat heartburn and/or acid reflux. One such band is described in U.S. Pat. No. 6,470,892 which is hereby incorporated herein by reference. Bands can also be used to treat impotence. One such band is described in U.S. Patent Application 2003/0114729 which is hereby incorporated herein by reference.

While preferred embodiments of the present invention have been shown and described herein, it will be obvious to those skilled in the art that such embodiments are provided by way of example only. Numerous variations, changes, and substitutions will now occur to those skilled in the art without departing from the invention. For example, as would be apparent to those skilled in the art, the disclosures herein have equal application in robotic-assisted surgery. In addition, it should be understood that every structure described above has a function and such structure can be referred to as a means for performing that function. Accordingly, it is intended that the invention be limited only by the spirit and scope of the appended claims.

What is claimed is:

1. A method for implanting an injection port within a patient, wherein the injection port comprises a housing having a closed distal end, a open proximal end, a fluid reservoir therebetween, a needle penetrable septum attached to said housing about said opening, and at least one attachment mechanism mounted to said housing at a pivot point along an outer periphery of said housing, wherein the injection port defines a central axis passing through the septum, the reservoir, and the housing, said attachment mechanism comprising an arcuate hook pivotable with respect to said housing, said arcuate hook having a length extending substantially at least 180° about said pivot point, said method comprising:
  a. creating an incision in the skin of a patient to expose the fascia;
  b. placing said distal end of said port adjacent the fascia;
  c. rotating said arcuate hook at least 180 degrees so that a free end of said hook extends into the fascia, back out again, and positioning the free end of said hook proximal to a distal end of said housing, wherein the act of rotating the hook comprises rotating the hook along a plane extending outwardly from the central axis of the injection port, wherein the act of rotating the hook further comprises rotating a sharp tip of the hook from a first position to a second position, second position is closer to the first position;
  d. closing the incision so that said hook remains within said patient; and
  e. coupling the injection port with a gastric band.

2. The method of claim 1 further comprising the step of attaching said port to a catheter tube.

3. The method of claim 2 further comprising the step of adding fluid to said port.

4. The method of claim 2 further comprising the step of withdrawing fluid from said port.

5. The method of claim 1, wherein the housing defines a generally circular outer periphery.

6. The method of claim 1, wherein the housing defines a recess configured to receive the free end of said arcuate hook.

7. The method of claim 6, wherein the act of positioning the free end of said hook proximal to a distal end of said housing comprises positioning the free end of said hook within said recess.

8. The method of claim 6, wherein the recess is defined in part by a substantially flat surface.

9. The method of claim 8, wherein the act of positioning the free end of said hook proximal to a distal end of said housing comprises positioning the free end of said hook within said recess such that the free end of said hook engages the substantially flat surface.

10. The method of claim 1, wherein the attachment mechanism comprises a plurality of arcuate hooks, each hook being pivotable with respect to said housing.

11. The method of claim 1, wherein the act of rotating said arcuate hook at least 180 degrees comprises rotating said arcuate hook along a path defined by a constant radius.

12. The method of claim 1, wherein the act of rotating said arcuate hook at least 180 degrees comprises driving said arcuate hook with forceps.

13. The method of claim 1, wherein the act of closing the incision comprises sewing the incision closed.

14. A method for implanting an injection port within a patient, wherein the injection port comprises a housing having a closed distal end, a open proximal end, a fluid reservoir therebetween, a needle penetrable septum attached to said housing about said opening, and at least one attachment mechanism mounted to said housing at a pivot point along an outer periphery of said housing, said attachment mechanism comprising an arcuate hook pivotable with respect to said housing, said arcuate hook having a length extending substantially at least 180° about said pivot point, said method comprising:
  a. creating an incision in the skin of a patient to expose the fascia;
  b. placing said distal end of said port adjacent the fascia;
  c. rotating said arcuate hook at least 180 degrees so that a free end of said hook extends into the fascia, back out again, and positioning the free end of said hook proximal to a distal end of said housing, wherein the housing defines a recess configured to receive the free end of said arcuate hook, wherein the act of rotating the hook comprises rotating the hook about an axis that is tangential to the housing, wherein the act of rotating the hook further comprises rotating the free end first away from an interior region of the housing then back toward the interior region of the housing;
  d. connecting said port to an adjustable gastric band via a catheter tube; and
  e. closing the incision so that said hook remains within said patient.

15. The method of claim 14 further comprising the step of adding fluid to said port.

16. The method of claim 14 further comprising the step of withdrawing fluid from said port.

17. The method of claim 14, wherein the act of positioning the free end of said hook proximal to a distal end of said housing comprises positioning the free end of said hook within said recess such that the free end of said hook engages a substantially flat surface of said recess.

18. A method of implanting an injection port within a patient, wherein the injection port comprises a housing defining a fluid reservoir, the injection port further comprising a fastener pivotally coupled with the housing, wherein the fastener comprises an arcuate hook having a free end, wherein the injection port defines a central axis passing through the septum, the reservoir, and the housing, the method comprising:
  a. creating an incision in the patient to provide access to tissue;
  b. placing the housing adjacent to the tissue;
  c. rotating the arcuate hook to secure the arcuate hook within the tissue, thereby securing the housing relative to the tissue, wherein the act of rotating the arcuate hook comprises passing the free end of the arcuate hook into a tissue entry site then back out of the tissue at a tissue exit site such that the free end of the arcuate hook is outside the tissue while an intermediate portion of the arcuate hook remains in the tissue upon completion of the act of rotating the arcuate hook, exit site is closer to the entry site, and wherein the arcuate hook has a length extending substantially at least about 180 degrees about the pivot point; and
  d. closing the incision such that the housing and the arcuate hook remain within the patient.

19. The method of claim 18, wherein the act of rotating the arcuate hook further comprises rotating the arcuate hook along an angular range spanning at least about 180 degrees.

* * * * *